Figure 1:
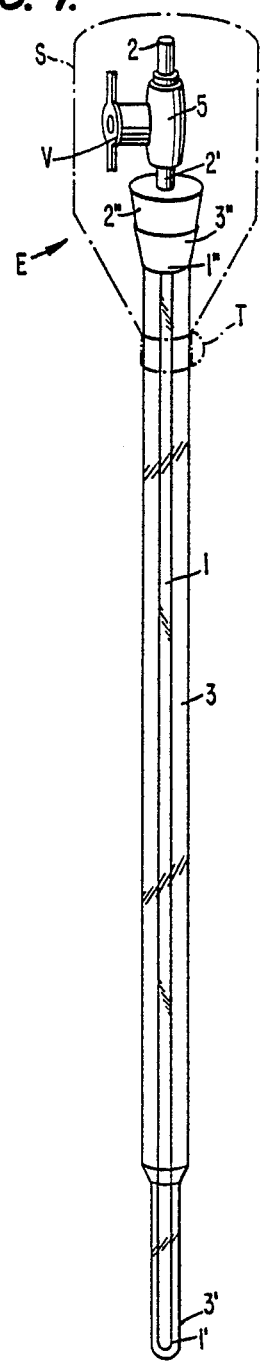

United States Patent [19]

McDonough

[11] Patent Number: 4,898,586
[45] Date of Patent: Feb. 6, 1990

[54] SUCTION CATHETER AND STORAGE HOLDER AND PACKAGE

[75] Inventor: Suellen McDonough, Durham, N.H.

[73] Assignee: The Academy of Applied Science, N.H.

[21] Appl. No.: 122,374

[22] Filed: Nov. 19, 1987

[51] Int. Cl.$^4$ .............................................. A61M 5/00
[52] U.S. Cl. .................................... 604/171; 206/364
[58] Field of Search ............... 604/171, 164, 165, 167; 206/363–364

[56] References Cited

U.S. PATENT DOCUMENTS

| | | | |
|---|---|---|---|
| 3,154,080 | 10/1964 | Rowan et al. | 604/171 |
| 3,235,069 | 2/1966 | Bennett et al. | 206/364 |
| 3,606,001 | 9/1971 | Talonn et al. | 206/364 |
| 3,606,889 | 9/1971 | Arblaster | 604/171 |
| 3,794,042 | 2/1974 | De Klotz et al. | 604/171 |
| 3,796,211 | 3/1974 | Kohl | 604/171 |
| 3,937,220 | 2/1976 | Coyne | 206/364 |
| 4,136,681 | 1/1979 | Hon | 604/171 |
| 4,168,699 | 9/1979 | Hauser | 604/171 |
| 4,446,967 | 5/1984 | Halkyard | 206/364 |
| 4,453,936 | 6/1984 | Cassou | 206/364 |

FOREIGN PATENT DOCUMENTS

| | | | |
|---|---|---|---|
| 2317839 | 10/1974 | Fed. Rep. of Germany | 604/172 |
| 2847455 | 5/1979 | Fed. Rep. of Germany | 604/171 |

Primary Examiner—C. Fred Rosenbaum
Assistant Examiner—Kathleen A. Daley
Attorney, Agent, or Firm—Rines and Rines

[57] ABSTRACT

A novel suction catheter assembly received and removably stopper-sealed within an outer sheath holder adapted to be mounted in a fixed location to obviate inadvertent discharge of fluids after use and accidental slipping onto the floor and similar present-day mishaps.

6 Claims, 2 Drawing Sheets

SUCTION CATHETER AND STORAGE HOLDER AND PACKAGE

The present invention relates to suction catheters as of the type used to aspirate the lungs and bronchealk areas, the trachea and other internal body passages for such purposes as the removal of congesting or other fluids or mucus or the like; and more particularly to holders or packages therefor that improve sterile, clear and facile conditions of use.

Under present medical practice, such catheters are packaged in flexible paper or other sterilized envelopes or the like with a valve T-section connector, the outlet stem of which is inserted into an end of the catheter tube; the inlet stem being adapted to be inserted within a flexible suction hose when the package is opened and the catheter removed. Suitable finger-operated valves that enable suction to be applied to the catheter in use are described, for example, in U.S. Pat. No. 4,534,532.

Current technique for readying the catheter for emergency use generally involved either placing the package near the patient's head for fast opening or already opened at an end. Sometimes the T-section will be inserted in the suction hose and the opened package with catheter, or the withdrawn catheter placed under the pillow, draped over the bed railing or tucked in an adjacent drawer or the like, where, of course, it can and often does fall on the floor. After a use, fluids can readily spew out the open end of the catheter (unsanitary and perhaps dangerous in connection with communicable diseases), and the hanging on the bed railing or anesthetic table for a repeated use is subject to such mess and to inadvertent dropping.

In accordance with the present invention, all of these drawbacks are admirably overcome by a novel sheathing of the catheter both in the package and in use; permitting, also, the pre-hooking of the catheter to the suction hose in a fixed condition and storage location.

An object of the invention, accordingly, is to provide a new and improved suction catheter and storage holder and package therefor that obviates the problems of inadvertent fluid discharge, dropping on the floor, and other unclean conditions, enabling pre-hooking to suction in definite or fixed locations, as well.

Other and further objects will be explained hereinafter and are more particularly delineated in connection with the appended claims.

In summary, however, the invention embodies a suction catheter and storage holder having, in combination, a flexible catheter tube open at one end and connected at the other end to an outlet stem of a valve T-stem section connector, the inlet stem of which is connectable to a suction hose; a storage sheath, at least of the length of the catheter tube, open at one end and closed at the other end and of cross-section larger than that of the catheter tube for receiving the same therein and therealong; the outlet stem having an enlarged region of cross dimension sufficient to seal the said one end of the sheath when the catheter is fully inserted within the sheath. Preferred and best mode details and constructional features are later presented.

Figure 3:
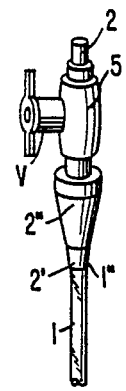
Figure 2:
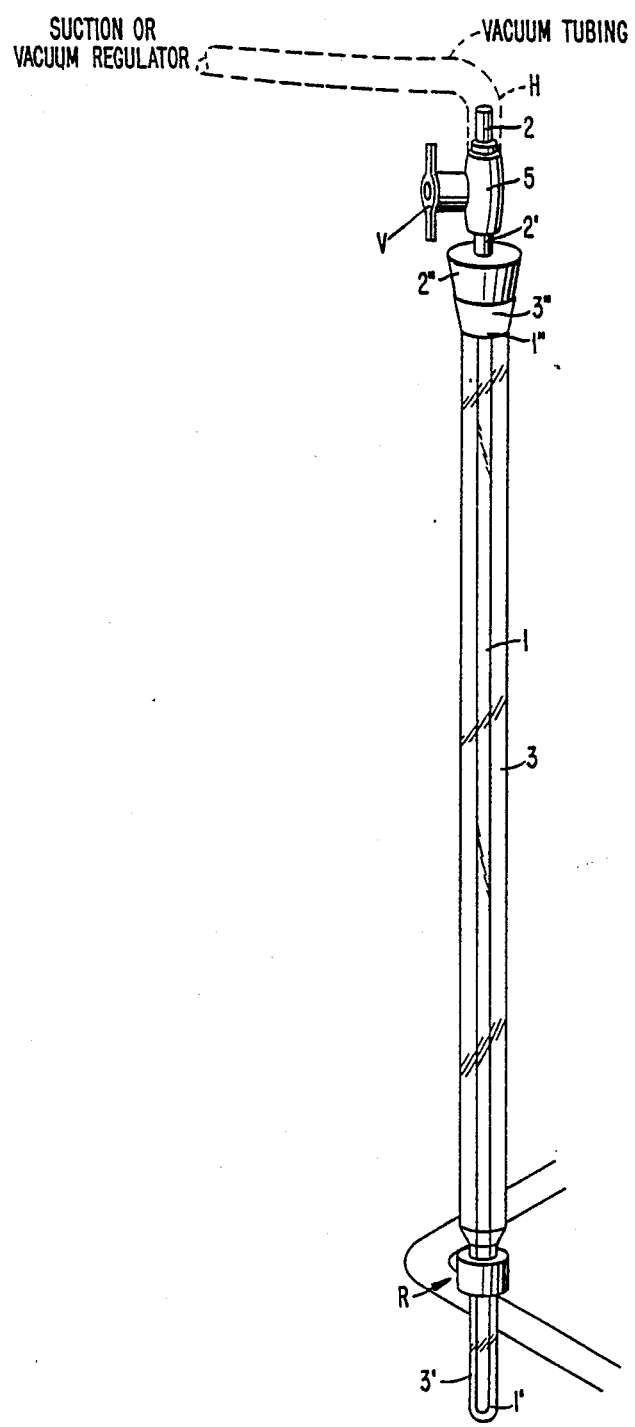

The invention will now be described with reference to the accompanying drawings, FIG. 1 of which is an isometric of a preferred catheter and storage holder combination, shown in the condition of sterile storage, as in an envelope package or the like;

FIG. 2 is a similar view showing the use of the catheter and holder in practice; and FIG. 3 is a partial view of a modified valve T-section member.

Referring to FIG. 1, the conventional flexible catheter tube 1, as of polyethylene tubing or other suitable, preferably transparent plastic material, is shown received and stored in surrounding holder storage sheat 3 of somewhat larger diameter and of length at least that of the catheter to accommodate the same with the lower open end 1' of the catheter at or near the lower sealed and 3' of the sheath 3. The sheath package 3 may be of thin-walled plastic tubing, also preferably transparent or translucent for observational purposes. It is shown at its upper normally open end provided with an outwardly flaring or tapering mouth 3", preferred, though not essential, for facile stoppering, as later explained.

A T-section connector 5, as of Teflon or other structurally similar plastic, is shown intermediately provided with a finger-operable valve V for closing or venting, or connecting section to the catheter 1 (when in use) from the inlet stem 2, as when the same is inserted within a suction or vacuum hose H, FIG. 2. The outlet stem 2' is shown inserted within the upper end 1" of the catheter 1, with an enlarged coaxially surrounding converging or tapering region 2" of sufficient cross-dimension to stopper-seal the mouth 3" of the sheath 2, with the catheter 1 contained therein.

This construction enables sterile storing and packaging of the catheter 1, being shown in FIG. 1 as provided with a sealed wrapper S, as of cellophane or Mylar sheeting or the like, removable by tearing a tape T binding the wrapper S to the upper outer wall of the sheath 3. The assembly may be wrapped in a conventional envelope package schematically designated at E.

In use, after removal of the wrapper S, the inlet 2, as before stated, is inserted and plugged within the suction or vacuum hose H. The construction of the present invention enables the fixed locating of the structure, as by inserting the reduced-diameter lower terminal section 2' of the sheath holder 3 within a receptacle R of, for example, an IV pole holder or stand available near the patient's head. This structure is thus adapted for fixed, pre-connection to the suction hose H and is readily usable (and re-usable) merely by withdrawing the valve T-section and stopper 2" with the pre-attached catheter 1 from the sheath 3. The same may be readily stored for repeated usages by re-inserting the catheter into the sheath holder, all without accidental discharge of fluids, dropping on the floor, or other disadvantageous effects of the prior art. When in use, the assembly is thus in a state of readiness without compromising cleanliness of the catheter portion of the product.

The enlarged stoppering or sealing member 2" may assume other forms than the external stopper of FIGS. 1 and 2. As another example, it may be shaped as at 2" in FIG. 3, having sufficient tapering cross-dimension inward of the T to seal the mouth 3" of the sheath holder 3, and terminating in the reduced diameter outlet section 2' that plugs into the upper end 1" of the catheter 1.

Further modifications will also occur to those skilled in the art, and such are considered to fall within the spirit and scope of the invention as defined in the appended claims.

What is claimed is:

1. A sterile suction catheter and sheath package in which the sheath serves also as a storage holder having, in combination, a flexible catheter tube open at one end and connected at the other end in an outlet stem of a valve T-stem section connector having inlet and outlet stems, the inlet stem of which is connectable to a suction hose; a packaging-and-storage sheath of tubing, in which the catheter is originally sterilely packaged end at least of the length of the catheter tube, open at one end and closed at the other end and of cross-section larger than that of the catheter tube for receiving the same therein and therealong; the said outlet stem having an enlarged region of cross dimension sufficient rigidly to seal within and against the said one end of the sheath when the catheter is fully inserted within the sheath and removable from said one end of the sheath to permit withdrawal of the catheter from the sheath, and then reinsertable within the sheath to re-seal within and against said one end of the sheath for repeated storage usage.

2. A suction catheter and storage holder as claimed in claim 1 and in which the outlet stem converges from the said enlarged region to a terminal region insertable within said other end of the catheter tube, with the converging wall thereof serving to stopper the said one end of the sheath.

3. A suction catheter and storage holder is claimed in claim 1 and in which the outlet stem is insertable within said other end of the catheter tube and is coaxially surrounded by a stopper for the said one end of the sheath.

4. A suction catheter and storage holder as claimed in claim 1 and in which a sterile removable seal wrapper encases the sealed end of the sheath and the valve stem.

5. A suction catheter and storage holder as claimed in claim 1 and in which the sheath is provided with means for enabling its support in a stand receptacle.

6. A suction catheter and storage holder as claimed in claim 1 and in which the support means is a reduced cross-section terminal section to hold the sheath in such receptacle.

* * * * *